US010155946B2

(12) United States Patent
Yehl et al.

(10) Patent No.: US 10,155,946 B2
(45) Date of Patent: Dec. 18, 2018

(54) PARTICLE-NUCLEIC ACID CONJUGATES AND THERAPEUTIC USES RELATED THERETO

(71) Applicant: Emory University, Atlanta, GA (US)

(72) Inventors: Kevin Yehl, Atlanta, GA (US); Salaita Khalid, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/728,474

(22) Filed: Oct. 9, 2017

(65) Prior Publication Data

US 2018/0057817 A1 Mar. 1, 2018

Related U.S. Application Data

(62) Division of application No. 14/403,211, filed as application No. PCT/US2013/027483 on Feb. 27, 2013, now Pat. No. 9,803,197.

(60) Provisional application No. 61/663,933, filed on Jun. 25, 2012.

(51) Int. Cl.

| | |
|---|---|
| A61K 48/00 | (2006.01) |
| C12N 15/113 | (2010.01) |
| C07H 21/02 | (2006.01) |
| C07H 21/04 | (2006.01) |
| C12N 15/87 | (2006.01) |
| C12N 15/11 | (2006.01) |
| A61K 45/06 | (2006.01) |
| A61N 5/06 | (2006.01) |
| A61K 47/69 | (2017.01) |
| A61K 47/52 | (2017.01) |
| C12Q 1/68 | (2018.01) |

(52) U.S. Cl.
CPC ............ *C12N 15/113* (2013.01); *A61K 45/06* (2013.01); *A61K 47/52* (2017.08); *A61K 47/6923* (2017.08); *A61N 5/062* (2013.01); *C07H 21/02* (2013.01); *C07H 21/04* (2013.01); *C12N 15/111* (2013.01); *C12N 15/87* (2013.01); *A61K 48/00* (2013.01); *C12N 2310/12* (2013.01); *C12N 2310/127* (2013.01); *C12N 2310/14* (2013.01); *C12N 2310/351* (2013.01); *C12N 2310/3511* (2013.01); *C12N 2320/51* (2013.01); *C12Q 1/68* (2013.01); *Y10T 428/2982* (2015.01); *Y10T 428/2991* (2015.01)

(58) Field of Classification Search
CPC . A61K 48/00; C12N 15/113; C12N 2310/127
See application file for complete search history.

(56) References Cited

U.S. PATENT DOCUMENTS

| | | | | |
|---|---|---|---|---|
| 9,803,197 | B2* | 10/2017 | Yehl | C12N 15/113 |
| 2009/0209629 | A1* | 8/2009 | Mirkin | A61K 9/5115 |
| | | | | 514/44 R |
| 2011/0229966 | A1* | 9/2011 | Han | A61K 31/7105 |
| | | | | 435/375 |
| 2012/0101267 | A1 | 4/2012 | Todd | |

FOREIGN PATENT DOCUMENTS

| | | |
|---|---|---|
| WO | 2011055888 | 5/2011 |
| WO | 2011108955 | 9/2011 |

OTHER PUBLICATIONS

Ryoo et al. (Biomaterials 33 (2012) 2754-2761, available online Dec. 27, 2011). (Year: 2011).*
Yang et al. (Chem. Commun. (2010) 46, 3107-3109). (Year: 2010).*
Hurst et al. (Anal. Chem. (2006) 78, 8313-8318). (Year: 2006).*
Naizov et al. (Nanoletters (2004) 4(9):1683-1687). (Year: 2004).*
Dass et al. DNAzyme technology and cancer therapy: cleave and let die, Mol Cancer Ther 2008, 7(2), 2008.
Giljohann et al., Gene Regulation with Polyvalent siRNA-Nanoparticle Conjugates, J. Am. Chem. Soc. 2009, 131, 2072.
Hurst et al, Maximizing DNA Loading on a Range of Gold Nanoparticle Sizes, Anal. Chem. (2006) 78, 8313-8318.
Liu et al., A Colorimetric Lead Biosensor Using DNAzyme-Directed Assembly of Gold Nanoparticles, Chem. Mater., 2003, 16, 3231-3238.
Liu et al. Colorimetric Lead Biosensor Using DNAzyme-Directed Assembly of Gold Nanoparticles, Journal of Fluorescence, vol. 14, No. 4, 2004.
Liu et al., DNAzyme-based fluorescent microarray for highly selective and sensitive detection of lead(II), Analyst, 2012, 137, 70-72, 2011.
Muller et al. Sensors made of RNA: tailored ribozymes for detection of small organic molecules, metals, nucleic acids and proteins, IEE Proc.-Nanobiotechnol., vol. 153, No. 2, 2006.
Niazov et al. DNAzyme-Functionalized Au Nanoparticles for the Amplified Detection of DNA or Teloerase Activity, Nano Letters, vol. 4, No. 9, 2004.
Niewiarowska et al., DNAzymes to mouse β1 integrin mRNA in vivo: targeting the tumor vasculature and retarding cancer growth, Cancer Gene Ther. 2009, 16 (9); 713-22.
Petree et al. Site-Selective RNA Splicing Nanozyme: DNAzyme and RtcB Conjugates on a Gold Nanoparticle, ACS 2, Chem. Biol. 13, 1, 215-224, 2018.

(Continued)

Primary Examiner — J. E. Angell
(74) Attorney, Agent, or Firm — Emory Patent Group

(57) ABSTRACT

This disclosure relates to particles conjugated to therapeutic nucleic acids. In certain embodiments, the nucleic acid comprises a sequence that catalytically cleaves RNA, e.g., DNAzyme or RNAzyme. In certain embodiments, the particles contain nucleic acids with both DNAzyme and/or RNAzyme and siRNA sequences. The cleaving nucleic acids optionally comprise a sequence functioning to hybridize to a target of interest and/or the particles are further conjugated to a targeting moiety. In certain embodiments, conjugated particles are used in the treatment or prevention of cancer or viral infections or bacterial infections. In certain embodiments, conjugated particles are used in detecting metal ions and other small molecule analyte.

18 Claims, 8 Drawing Sheets

Specification includes a Sequence Listing.

(56) References Cited

OTHER PUBLICATIONS

Pun et al. Targeted Delivery of RNA-Cleaving DNA Enzyme (DNAzyme) to Tumor Tissue by Transferrin-Modified, Cyclodextrin-Based Particles, Cancer Biology & Therapy 3:7, 641-650, 2004.
Rosi et al., Oligonucleotide-modified gold nanoparticles for intracellular gene regulation, Science 2006, 312, 1027.
Ruttkay et al. G-Quadruplexes as Sensing Probes, Molecules 2013, 18, 14760-14779.
Ryoo et al, Functional delivery of DNAzyme with iron oxide nanoparticles for hepatitis C virus gene knockdown, Biomaterials 33 (2012) 2754-2761.
Santiago et al., New DNA enzyme targeting EGR-1 mRNA inhibits vascular smooth muscle proliferation and regrowth after injury, Nature Med. 1999, 5: 1264-9.
Somasuntharam et al. Knockdown of TNF-α by DNAzyme Gold Nanoparticles as an Anti-inflammatory Therapy for Myocardial Infarction, Biomaterials. Mar. 2016; 83: 12-22.
Yang et al, A novel electrochemical DNAzyme sensor for the amplified detection of Pb2+ ions, Chem. Commun. (2010)46-3107-3109.
Zaborowska et al. Sequence Requirements in the Catalytic Core of the "10-23" DNA Enzyme, J Bio Chem, 277(43), 40617-40622, 2002.
Zhang et al., Angiogenic inhibition mediated by a DNAzyme that targets vascular endothelial growth factor receptor 2, Cancer Res. 2002, 62: 5463-9.
Extended European Search Report for EP Application No. 13808488.4 dated Dec. 21, 2015.
European Examination Report for EP Application No. 13808488.4 dated Jul. 19, 2017.

* cited by examiner

PARTICLE-NUCLEIC ACID CONJUGATES AND THERAPEUTIC USES RELATED THERETO

CROSS REFERENCE TO RELATED APPLICATIONS

This application is a division of U.S. application Ser. No. 14/403,211 filed Nov. 24, 2014, which the National Stage of International Application No. PCT/US2013/027843 filed Feb. 27, 2013, which claims priority to U.S. Provisional Application No. 61/663,933 filed Jun. 25, 2012. The entirety of each of these applications is hereby incorporated by reference for all purposes.

INCORPORATION-BY-REFERENCE OF MATERIAL AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11212USDIV_ST25.txt. The text file is 3 KB, was created on Oct. 9, 2017, and is being submitted electronically via EFS-Web.

FIELD

This disclosure relates to particles conjugated to therapeutic nucleic acids. In certain embodiments, the nucleic acid comprises a sequence that catalytically cleaves RNA, e.g., DNAzyme or RNAzyme. In certain embodiments, the particles contain nucleic acids with both DNAzyme and/or RNAzyme and siRNA sequences. The cleaving nucleic acids optionally comprise a sequence functioning to hybridize to a target of interest and/or the particles are further conjugated to a targeting moiety. In certain embodiments, conjugated particles are used in the treatment or prevention of cancer or viral infections or bacterial infections. In certain embodiments, conjugated particles are used in detecting metal ions and other small molecule analytes.

BACKGROUND

Nucleic acids such as siRNA and DNAzymes have been contemplated as active ingredients in therapeutic strategies. DNAzymes are short deoxyribonucleotide sequences that cleave target RNA sequences, e.g., mRNA. Small interfering RNA (siRNA) contains RNA sequences which are typically between 20-25 nucleotides in length. siRNA interferes with the expression of a specific gene containing the siRNA sequences. DNAzymes hold potential advantages over siRNA for therapeutic gene regulation due to their innate ability to catalytically cleave mRNA without the need for hijacking the RISC (RNA-induced Silencing Complex) machinery of the cell.

DNAzymes targeting mRNA of integrins reduced protein expression in endothelial cells and thus blocked microvascular endothelial cell capillary tube formation. See e.g., Niewiarowska et al., Cancer Gene Ther. 2009, 16(9):713-22. DNAzyme regulation of the EGFR gene expression levels was shown to inhibit the growth of cancer cells. See Santiago et al., Nature Med. 1999, 5:1264-9. DNAzymes that cleave VEGFR2 mRNA were shown to limit the proliferation of endothelial cells and blocked tumor growth in vivo. Zhang et al., Cancer Res. 2002, 62:5463-9.

The movement of nucleic acids to a site of interest within a cell presents a challenge to using nucleic acids as therapeutic agents. Cell membranes generally prevent nucleic acids from migrating in and out of cellular compartments. Cationic polymers or liposomes may be employed to improve delivery. Cationic liposomes are toxic to cells. Once within the cells, biological processes degrade oligonucleotides. Chemically modifying the oligonucleotide backbone can slow nuclease activity. In any case, there is exists a need to identify improved compositions and methods.

Liu & Lu disclose a gold nanoparticle/DNAzyme assembly for a biosensor application. See Chem. Mater., 2004, 16, 3231-3238. See also Yang et al., Chem Commun, 2010, 46, 3107-3109. Rosi et al., disclose oligonucleotide-modified gold nanoparticles for intracellular gene regulation. See Science 2006, 312, 1027. Giljohann et al., disclose gene regulation with polyvalent siRNA-nanoparticle conjugates. See J. Am. Chem. Soc. 2009, 131, 2072. See also Hurst et al., Anal. Chem., 2006, 78 (24):8313-8318 and Liu et al., Analyst, 2012, 137, 70-72. References cited herein are not an admission of prior art.

SUMMARY

This disclosure relates to particles conjugated to therapeutic nucleic acids. In certain embodiments, the nucleic acid comprises a sequence that catalytically cleaves RNA, e.g., DNAzyme or RNAzyme. In certain embodiments, the particles contain nucleic acids with both DNAzyme and/or RNAzyme and siRNA sequences. The cleaving nucleic acids optionally comprise a sequence functioning to hybridize to a target of interest and/or the particles are further conjugated to a targeting moiety. In certain embodiments, conjugated particles are used in the treatment or prevention of cancer or viral infections or bacterial infections. In certain embodiments, conjugated particles are used in detecting metal ions and other small molecule analytes.

In certain embodiments, the diameter of the particle is about 500 nm to 5 nm or 200 nm to 10 nm or 5 nm. In certain embodiments, the particle comprises or consists essentially of a metal such as gold, silver, iron, or iron oxide.

In certain embodiment, the disclosure contemplates cleaving nucleic acids which are DNAzymes that cleave RNA, e.g. mRNA or viral or bacterial RNA or mRNA. In certain embodiments, the DNAzyme may cleave RNA independent of metal cations. In certain embodiments, the cleaving nucleic acid is selected from DNAzyme 10-23, DNAzyme 20-49, and DNAzyme 8-17 or variants or modified forms thereof such as amine or imidazolyl modified deoxyadenosines. In certain embodiments, the cleaving nucleic acid is DNAzyme 10-23 coating the particle at about one nucleic acid to about 3 to 12 square nanometers of the particle surface. In certain embodiments, the cleaving nucleic acid is DNAzyme 10-23 coating the particle at about or greater than 8, 9, 10, or 11 square nanometers per nucleic acid or less than 12 or 15 square nanometers per nucleic acid.

In certain embodiments, the particle is conjugated to the nucleic acid through a linking group comprising a thiol group, metal ligand, ethylene glycol polymer, alkyl chain, ester group, or amide group. In certain embodiments, a metal particle is coated with a polymer and the nucleic acid is conjugated to the polymer. In certain embodiment, the particle is further conjugated to a targeting moiety and/or siRNA.

In certain embodiments, the disclosure relates to methods comprising administering a pharmaceutical composition comprising a particle conjugate disclosed herein to a subject in need thereof. In certain embodiments, the subject is diagnosed with cancer, a viral infection, or a bacterial infection.

In certain embodiments, the disclosure relates to the production of a medicament or pharmaceutical composition comprising particles disclosed herein and a pharmaceutically acceptable excipient for use in treating cancer or a viral or bacterial infection. Typically, the pharmaceutical composition is in the form of a buffered saline solution, capsule, pill, or tablet.

In certain embodiments, conjugated particles are used in detecting metal ions and other small molecule analytes. In certain embodiments, the disclosure relates to methods of mixing particles disclosed herein and a sample containing metal ions or other molecules that bind nucleic acids on the particles and measuring binding.

It is to be understood that both the foregoing general description and the following detailed description are exemplary and explanatory only and are not restrictive of the disclosure, as claimed.

DETAILED DESCRIPTION

Figure 1A:
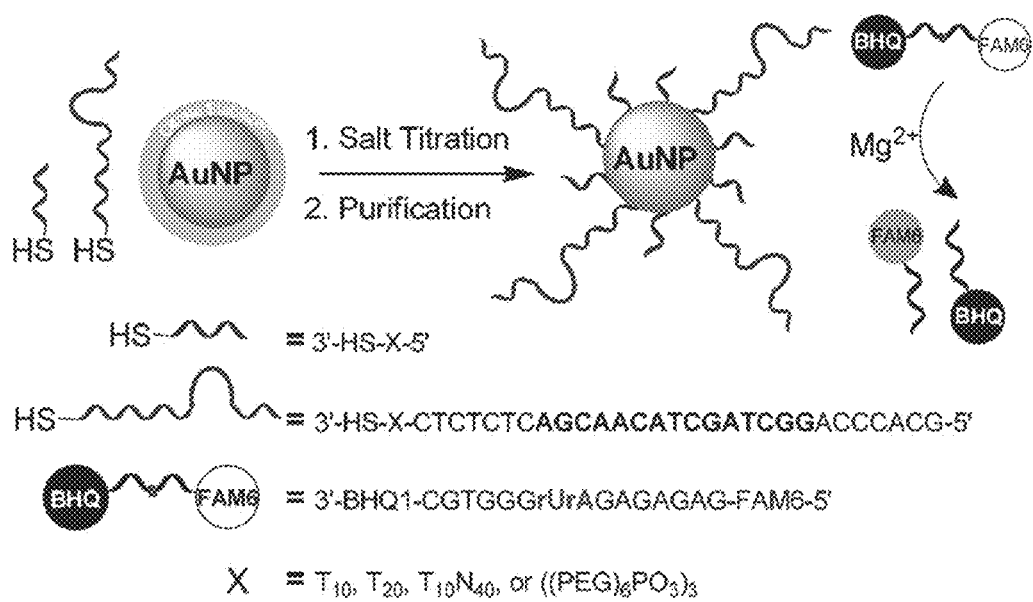
FIG. 1A schematically illustrates DzNP synthesis and catalysis strategy used to generate DNAzyme-AuNP conjugates (DzNPs). A binary mixture of two oligonucleotides, DNAzymes and pas-sivating strands, were used to control the steric environment at the particle surface. The catalytic activity of DzNPs was deter-mined by measuring the rate of fluorescence increase, which represents the rate of substrate hydrolysis and de-quenching. The cleaving activity of DzNPs was determined by measuring the rate of fluorescence increase, which represents the rate of substrate hydrolysis and de-quenching. 10-23 DNAzyme is 3'-AG-CAACATCGATCGG-5' (SEQ ID NO:1) which is within 3'-TCTCTCAGCAACATCGATCGGACCCACG-5' (SEQ ID NO: 2) which hybridizes and cleaves 3' -CGTGGGrU-rAGAGAGAG-5' (SEQ ID NO: 3).

This disclosure relates to particles conjugated to therapeutic nucleic acids. In certain embodiments, the nucleic acid comprises a sequence that catalytically cleaves RNA, e.g., DNAzyme or RNAzyme. In certain embodiments, the particles contain nucleic acids with both DNAzyme and/or RNAzyme and siRNA sequences. The cleaving nucleic acids optionally comprise a sequence functioning to hybridize to a target of interest and/or the particles are further conjugated to a targeting moiety. In certain embodiments, conjugated particles are used in the treatment or prevention of cancer or viral infections or bacterial infections. In certain embodiments, conjugated particles are used in detecting metal ions and other small molecule analytes.

Particles Conjugated to Cleaving Nucleic Acids

In certain embodiments, the disclosure relates to particles conjugated to a cleaving nucleic acid wherein the nucleic acid comprises a sequence that cleaves RNA. Single-stranded nucleic acids can fold into tertiary structures and act as catalysis similar to enzymes made of protein. Ribozymes, RNAzymes, and deoxyribozymes, DNAzymes, have been isolated from naturally occurring molecules and optimized from random-sequence populations using in vitro selection. A combinatorial strategy may be used to create numerous classes of nucleic acid-cleaving DNAzymes and RNAzymes. DNAzymes and RNAzymes often, but not exclusively, catalyze cleavage of the RNA 3',5'-phosphodiester linkage by promoting an internal transesterification reaction to produce 2',3'-cyclic phosphate and 5'-hydroxyl termini.

In certain embodiments, the disclosure relates to particles conjugated to a cleaving nucleic acid such as DNAzyme 10-23. The DNAzyme 10-23 is comprised of a sequence of DNA that will cleave mRNA strands that contain an unpaired purine-pyrimidine pair. The DNAzyme 10-23 is typically flanked by a recognition sequence that will specifically recognize a short region of the target mRNA. Therefore, the DNAzyme will recognize the complementary mRNA, hybridize, cleave at a site, and consequently alter the expression of protein targets.

In certain embodiments, this disclosure contemplates that the cleaving nucleic acids comprise sequences of DNAzymes 8-17 and 10-23. Santoro & Joyce disclosed a general purpose RNA-cleaving DNAzymes 8-17 and 10-23. See PNSA, 1997, 94 (9), 4262-4266, hereby incorporated by reference.

In certain embodiments, this disclosure contemplates that the cleaving nucleic acids comprise 8-imidazolyl modified deoxy adenosines RNaseA mimicking DNAzymes. Perrin et al., disclose modified DNAzymes 20-49 containing amine, guanidine, and imidazole-modified dNTPs. Org Biomol Chem 2011, 9 (7), 2266-2273, hereby incorporated by reference.

In certain embodiments, this disclosure contemplates that the cleaving nucleic acids is DNAzyme pH5DZ1. Li et al., disclose DNAzymes pH5DZ1. See Biochemistry, 2009, 48 (31):7383-7391, hereby incorporated by reference. Li et al, also disclose DNAzyme classes with large catalytic domains (>40 nucleotides) utilizing three-way or four-way junction structural frameworks. See Mol Biosyst 2011, 7 (7), 2139-2146, hereby incorporated by reference.

In certain embodiments, the cleaving nucleic acid is 10MD9, 10MD1, 10MD14, and 10MD5. Chandra et al., disclose 10MD9, 10MD1, 10MD14, and 10MD5. See Nat Chem Biol 2009, 5 (10), 718-720, hereby incorporated by reference.

In certain embodiments, the cleaving nucleic acid is a bipartite DNAzyme. Feldman and Sen disclose bipartite DNAzymes suitable for the sequence-specific cleavage of RNA. See J Mol Biol 2001, 313 (2): 283-294 and Chembiochem, 2006, 7 (1): 98-105, hereby incorporated by reference.

In certain embodiments, the cleaving nucleic acid is a DNAzyme of the Na family. A DNAzyme of the Na family generally contains a consensus sequence ACCCAAGAAGGGGTG (SEQ ID NO:4). In certain embodiments, the cleaving nucleic acid comprises SEQ ID NO:4 and GCX$^1$TX$^2$ACX$^3$X$^4$X$^5$AT (SEQ ID NO:5) wherein X is any amino acid. Geyer & Sen disclose DNAzymes of the Na family. See Chem Biol, 1997, 4 (8): 579-593, hereby incorporated by reference.

In certain embodiments, the cleaving nucleic acid is a DNAzyme HD2. Breaker & Roth disclose HD2. See. PNAS, 1998, 95 (11): 6027-6031, hereby incorporated by reference In certain embodiments, the cleaving nucleic acid is a DNAzyme pH3Dz1. Li et al., disclose pH3DZ1. See Can J Chem 2007, 85 (4), 261-273, hereby incorporated by reference.

In certain embodiments, the cleaving nucleic acid is a DNAzyme comprising AATTCCGTAGGTCCAGTG (SEQ ID NO:6) and ATCTCCTCCTGTTC (SEQ ID NO:7). Adriaens and Vannela disclosed RNA-cleaving DNAzymes containing SEQ ID NO: 6 and SEQ ID NO:7. See Environ Eng Sci 2007, 24 (1), 73-84, hereby incorporated by reference.

In certain embodiments, the cleaving nucleic acid is DNAzyme MG5. Peracchi disclosed DNAzyme MG5 deoxyribozyme. See J Biol Chem 2000, 275 (16), 11693-11697, hereby incorporated by reference.

In certain embodiments, the cleaving nucleic acid is DNAzyme 17E. In certain embodiments, the cleaving nucleic acid comprises X3AGCY3TCGAA (SEQ ID NO: 8), or TX$_3$AGCY$_3$TCGAAATAGT (SEQ ID NO: 9) wherein X$_3$ and Y$_3$ are complimentary. Li et al., disclose DNAzyme 17E and other variants. See Nucleic Acids Res, 2000, 28 (2), 481-488, hereby incorporated by reference.

In certain embodiments, the cleaving nucleic acid is DNAzyme 614. Carrigan et al., disclosed DNAzyme 614. See Biochemistry, 2004, 43 (36), 11446-11459, hereby incorporated by reference.

In certain embodiments, the cleaving nucleic acid comprises a segment that hybridizes to mRNA of EGR-1. Fahmy et al., disclose DNAzymes targeting early growth response (EGR-1) mRNA. See Nat Med 2003, 9 (8), 1026-1032 and Santiago et al., Nat Med, 1999, 5 (12), 1438-1438, both hereby incorporated by reference. In certain embodiments, the cleaving nucleic acid comprises a segment that hybridizes to human EGR-1 mRNA. Mitchell et al., disclose a DNAzyme targeting EGR-1. See Nucleic Acids Res 2004, 32 (10), 3065-3069, hereby incorporated by reference.

In certain embodiments, the cleaving nucleic acid comprises a segment that hybridizes to c-Jun mRNA, e.g., Dz13. Zhang et al., disclose deoxyribozymes targeting c-Jun. See J Biol Chem 2002, 277 (25), 22985-22991, J Natl Cancer I 2004, 96 (9), 683-696, and Oncogene 2006, 25 (55), 7260-7266, all hereby incorporated by reference. Fahmy et al., disclose DNAzyme Dz13 that cleaves human c-Jun mRNA. See Nat Biotechnol 2006, 24 (7), 856-863, hereby incorporated by reference.

In certain embodiments, the cleaving nucleic acids comprise a segment that hybridizes to LMP1 mRNA. Lu et al., disclose EBV LMP1 targeted DNAzymes. See Cancer Gene Ther 2005, 12 (7), 647-654, hereby incorporated by reference.

In certain embodiments, the cleaving nucleic acid comprises a segment that hybridizes to hepatitis B virus X gene open reading frame. Hou et al., disclose inhibition of hepatitis B virus X gene expression by a DNAzymes10-23. See Antivir Res 2006, 72 (3), 190-196, hereby incorporated by reference.

In certain embodiments, the cleaving nucleic acid comprises a segment that hybridizes to RNA sequences encoding the HCV core protein Trepanier et al., disclose cleavage of intracellular hepatitis C RNA in the virus core protein coding region by deoxyribozymes. See J Viral Hepatitis 2006, 13 (2), 131-138, hereby incorporated by reference.

In certain embodiments, the cleaving nucleic acid comprises a segment that hybridizes to HIV RNA sequences, e.g., encoding HIV-1 gag, nef, rev, env or tat. Sriram & Banerjea disclose DNAzymes interference with HIV-1-specific gene expression. See Biochem J 2000, 352, 667-673, hereby incorporated by reference. See also Dash & Banerjea, Oligonucleotides 2004, 14 (1), 41-47, Sood et al., Oligonucleotides 2007, 17 (1), 113-121, and Unwalla et al., Antivir Res 2006, 72 (2), 134-144, Sood et al., Aids 2007, 21 (1), 31-40, and Jakobsen et al., Retrovirology 2007, 4, all hereby incorporated by reference.

In certain embodiments, the cleaving nucleic acid comprises a segment that hybridizes to mRNA of human telomere reverse transcriptase. Yuan et al., disclose DNAzymes targeting the telomerase mRNA. See Int J Biochem Cell B 2007, 39 (6), 1119-1129, hereby incorporated by reference.

In certain embodiments, the cleaving nucleic acid comprises a segment that hybridizes to mRNA of influenza virus, e.g., PB2 mRNA of influenza A. Takahashi et al., disclose DNAzymes that targets influenza virus A mRNA. See Febs Lett 2004, 560 (1-3), 69-74, hereby incorporated by reference.

In certain embodiments, the cleaving nucleic acid comprises a segment that hybridizes to mRNA mycobacterium tuberculosis, e.g., mRNA of Isocitrate lyase (ICL). Li et al., disclose DNAzymes targeting the id gene. See Oligonucleotides 2005, 15 (3), 215-222, hereby incorporated by reference.

In certain embodiments, the cleaving nucleic acid comprises a segment that hybridizes to bacterial mRNA, e.g., beta-lactamase mRNA. Chen et al., disclose DNAzymes targeted to beta-lactamase mRNA. See Oligonucleotides 2004, 14 (2), 80-89, hereby incorporated by reference. See also Hou et al., Acta Pharmacol Sin 2007, 28 (11), 1775-1782, hereby incorporated by reference.

In certain embodiments, the cleaving nucleic acid comprises a segment that hybridizes to human platelet type 12 lipoxygenase mRNA. Liu et al., disclose cleaving DNAzyme to mRNA of platelet-type 12-lipoxygenase. See Biochem Bioph Res Co 2001, 284 (4), 1077-1082, hereby incorporated by reference.

In certain embodiments, the cleaving nucleic acid comprises a segment that hybridizes to the translation initiation region of c-myc RNA. Sun et al., disclose a DNAzyme targeting c-myc RNA. See J Biol Chem 1999, 274 (24), 17236-17241, hereby incorporated by reference. See also, Pun et al., Cancer Biol Ther 2004, 3 (7), 641-650, hereby incorporated by reference.

In certain embodiments, the cleaving nucleic acid comprises a 3' end modified such that last two nucleotides are connected by a phosphodiester linkage between the 3' positions of each nucleotides. See Dass et al., Nucleic A 2002, 12 (5), 289-299, hereby incorporated by reference.

In certain embodiments, the cleaving nucleic acid comprises a segment that hybridizes to ornithine decarboxylase (ODC). Ackermann et al., disclose DNAzyme to ornithine decarboxylase mRNA. See Biochemistry, 2005, 44 (6), 2143-2152, hereby incorporated by reference.

In certain embodiments, the cleaving nucleic acid comprises a segment that hybridizes to MecR1 mRNA, e.g., PS-DRz147. Hou et al., disclosed PS-DRz147. See Acta Pharmacol Sin 2006, 27, 59-59, hereby incorporated by reference In certain embodiments, the cleaving nucleic acid comprises a segment that hybridizes to genomic RNA sequence of the RSV nucleocapsid protein, e.g., DZ1133. Zhou et al., disclose DNAzyme DZ1133. See Virus Res 2007, 130 (1-2), 241-248, hereby incorporated by reference.

In certain embodiments, the cleaving nucleic acid comprises a segment that hybridizes to the loop region of the 5'UTR of SARS-CoV, e.g., Dv-104. Wu et al., disclose that DNAzyme, DZ-104 can specifically target the 5'-untranslated region of severe acute respiratory syndrome associated coronavirus (SARS-CoV). See J Gene Med 2007, 9 (12), 1080-1086, hereby incorporated by reference.

In certain embodiments, the cleaving nucleic acid comprises a segment that hybridizes to survivin mRNA. Liang et al., disclose DNAzyme cleavage of survivin mRNA. See J Gastroen Hepatol 2005, 20 (10), 1595-1602, hereby incorporated by reference.

In certain embodiments, the cleaving nucleic acid comprises a segment that hybridizes to TGF-beta mRNA. See Isaka et al., disclose DNAzyme for TGF-beta. See Kidney Int, 2004, 66 (2), 586-590, hereby incorporated by reference.

In certain embodiments, the cleaving nucleic acid comprises a segment that hybridizes to Twist mRNA. Hjiantoniou et al., disclose DNazyme-mediated cleavage of Twist transcripts. See Biochem Bioph Res Co 2003, 300 (1), 178-181, hereby incorporated by reference.

In certain embodiments, the cleaving nucleic acid comprises a segment that hybridizes to mRNA of VEGFR2. Zhang et al., discloses a DNAzyme that targets vascular endothelial growth factor receptor 2. See Cancer Res 2002, 62 (19), 5463-5469, hereby incorporated by reference.

Therapeutic Applications and Combination Therapies

In certain embodiments, the disclosure relates to pharmaceutical compositions comprising particle conjugates disclosed herein for administration to a subject for the prevention or treatment of a condition or disease. In certain embodiments, the disclosure relates to methods of treating or preventing cancer or a viral infection or a bacterial infection comprising administering an effective amount of a pharmaceutical composition disclosed herein to a subject.

In certain embodiments, the subject may be diagnosed with a cancer, at risk of cancer, diagnosed with a tumor. In certain embodiments, the cancer is selected from brain, lung, cervical, ovarian, colon, breast, gastric, skin, ovarian, pancreatic, prostate, neck, and renal cancer.

In some embodiments, the pharmaceutical composition is administered in combination with a second anticancer agent, and the second anticancer agent may be selected from temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

In certain embodiment, the pharmaceutical composition is administered in combination with an siRNA.

In certain embodiment, the subject may be pre- or postoperatively provided radiation therapy. In certain embodiments, contemplated methods comprise administering the particle conjugated and utilizing phototherapy, e.g., releasing the attached nucleic acid in a target area of the by exposing the subject to electromagnetic radiation under conditions such that the administered particle releases nucleic acids conjugated to the particle.

In certain embodiments, the subject may be diagnosed with a viral or bacterial infection, at risk of viral or bacterial infection, or exhibiting symptoms of a viral or bacterial infection. In certain embodiments, the subject is diagnosed with an RNA based viral infection, e.g., an RNA virus, or utilizes an RNA intermediated.

In some embodiments, the subject is diagnosed with influenza A virus including subtype H1N1, influenza B virus, influenza C virus, rotavirus A, rotavirus B, rotavirus C, rotavirus D, rotavirus E, SARS coronavirus, human adenovirus types (HAdV-1 to 55), human papillomavirus (HPV) Types 16, 18, 31, 33, 35, 39, 45, 51, 52, 56, 58, 59, parvovirus B19, molluscum contagiosum virus, JC virus (JCV), BK virus, Merkel cell polyomavirus, coxsackie A virus, norovirus, Rubella virus, lymphocytic choriomeningitis virus (LCMV), yellow fever virus, measles virus, mumps virus, respiratory syncytial virus, rinderpest virus, California encephalitis virus, hantavirus, rabies virus, ebola virus, marburg virus, herpes simplex virus-1 (HSV-1), herpes simplex virus-2 (HSV-2), varicella zoster virus (VZV), Epstein-Barr virus (EBV), cytomegalovirus (CMV), herpes lymphotropic virus, roseolovirus, Kaposi's sarcoma-associated herpesvirus, hepatitis A (HAV), hepatitis B (HBV), hepatitis C (HCV), hepatitis D (HDV), hepatitis E (HEV), human immunodeficiency virus (HIV), The Human T-lymphotropic virus Type I (HTLV-1), Friend spleen focus-forming virus (SFFV) or Xenotropic MuLV-Related Virus (XMRV).

In some embodiments, the subject is diagnosed with gastroenteritis, acute respiratory disease, severe acute respiratory syndrome, post-viral fatigue syndrome, viral hemorrhagic fevers, acquired immunodeficiency syndrome, or hepatitis.

In some embodiments, the disclosure relates to treating a viral infection by administering a composition comprising particles disclosed herein in combination with a second antiviral agent, e.g., abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, imunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine. In certain embodiments, the subject is administered a pharmaceutical composition comprising particles disclosed herein and a second antiviral agent.

In certain embodiments, the subject is treated for a bacterial infection in combination with another antibiotic such as sulphadiazine, sulfones—[dapsone (DDS) and paraaminosalicyclic (PAS)], sulfanilamide, sulfamethizole, sulfamethoxazole, sulfapyridine, trimethoprim, pyrimethamine, nalidixic acids, norfloxacin, ciproflaxin, cinoxacin, enoxacin, gatifloxacin, gemifloxacin, grepafloxacin, levofloxacin, lomefloxacin, moxifloxacin, ofloxacin, pefloxacin, sparfloxacin, trovafloxacin, penicillins (amoxicillin, ampicillin, azlocillin, carbenicillin, cloxacillin, dicloxacillin, flucloxacillin, hetacillin, oxacillin, mezlocillin, penicillin G, penicillin V, piperacillin), cephalosporins (cefacetrile, cefadroxil, cefalexin, cefaloglycin, cefalonium, cefaloridin, cefalotin, cefapirin, cefatrizine, cefazaflur, cefazedone, cefazolin, cefradine, cefroxadine, ceftezole, cefaclor, cefonicid, ceforanide, Cefprozil, cefuroxime, cefuzonam, cefmetazole, cefoteta, cefoxitin, cefcapene, cefdaloxime, cefdinir, cefditoren, cefetamet, cefixime, cefmenoxime, cefodizime, cefoperazone, cefotaxime, cefotiam, cefpimizole, cefpiramide, cefpodoxime, cefteram, ceftibuten, ceftiofur, ceftiolen, ceftizoxime, ceftriaxone, cefoperazone, ceftazidime, cefepime), moxolactam, carbapenems (imipenem, ertapenem, meropenem), monobactams (aztreonam), oxytetracycline, chlortetracycline, clomocycline, demeclocycline, tetracycline, doxycycline, lymecycline, meclocycline, methacycline, minocycline, rolitetracycline, chloramphenicol, amikacin, gentamicin, framycetin, kanamycin, neomicin, neomycin, netilmicin, streptomycin, tobramycin, azithromycin, clarithromycin, dirithromycin, erythromycin, roxithromycin, telithromycin, polymyxin-B, colistin, bacitracin, tyrothricin notrifurantoin, furazolidone, metronidazole, tinidazole, isoniazid, pyrazinamide, ethionamide, nystatin, amphotericin-B, hamycin, miconazole, clotrimazole, ketoconazole, fluconazole, rifampacin, lincomycin, clindamycin, spectinomycin, chloramphenicol, clindamycin, colistin, fosfomycin, loracarbef, metronidazole, nitrofurantoin, polymyxin B, polymyxin B sulfate, procain, spectinomycin, tinidazole, trimethoprim, ramoplanin, teicoplanin, vancomycin, trimethoprim, sulfamethoxazole, and/or nitrofurantoin.

Metal Particles, Coatings, and Preparation

This disclosure relates to particles conjugated to a cleaving nucleic acid wherein the nucleic acid comprises a sequence that cleaves RNA, e.g., DNAzyme or RNAzyme. In certain embodiments, the particle comprises or consists essentially of a metal such as gold, silver, iron, or iron oxide. Typically, the particle is a metal nanoparticle. In some embodiments, the cleaving nucleic acid is conjugated to the metal particle through surface coated polymer.

Contemplated particles include pegylated colloidal gold and iron oxide nanoparticles. See Qian et al., Nature Biotechnology, 2008, 26, 83-90, Hadjipanayis et al., Cancer Research, 2010, 70(15):6303-6312, and Peng et al., Int J Nanomedicine. 2008 September; 3(3): 311-321, all hereby incorporated by reference. A couple of approaches may be used for the chemical synthesis of contemplated gold nanoparticles. Alkanethiols may be used to stabilize gold particles. See, e.g., Brust et al., J Chem Soc, Chem Commun, 1994, 801-02 and Templeton et al., Acc Chem Res, 2000, 33, 27, all hereby incorporated by reference. In another approach, one uses sodium citrate as a reducing agent and stabilizing ligand. See Turkevich et al., Discuss Faraday Soc, 1951, 11, 55, hereby incorporated by reference. The particle size can be controlled by the gold precursor/citrate molar ratio. Kairdolf & Nie disclose the production of multidentate-protected colloidal gold nanoparticles. See J. Am. Chem. Soc. 2011, 133, 7268-7271, hereby incorporated by reference.

Nanoparticles are typically prepared with a mean particle diameter of 4-100 nm. Iron-oxide nanoparticles (IONPs) may be prepared by aging a stoichiometric mixture of ferrous and ferric salts in aqueous media under basic conditions. Control over particle size (2-20 nm) and shape is provided by adjusting the pH, ionic strength and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm) can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, $ZrO_2$, silica, etc.) as well as hybrid particles (e.g. silica-IONPs).

Hydroxyl groups on the IONP provide a place for synthetic attachment of different functional groups. A range of chemistries can be used to stabilize metal nanoparticles, exploiting electrostatic, hydrophobic, chelating and covalent interactions. Carboxylic acid groups can interact with the surface of IONPs by coordination processes. IONP synthesis in organic solvents is typically conducted in oleic acid. A polymer coating on the IONPs is preferred. Polymer attachment to the IONP surface by an initiator fixed to the surface of the IONPs and the polymer is grown from the surface. Alternatively, a functional, pre-formed polymer is grafted onto IONPs in situ. Copolymers with hydrophobic groups, carboxylic acid groups, polyethylene glycols, or amine groups are contemplated.

Conjugating cleaving nucleic acids to the polymers can be accomplished using a variety of methods. For example, a primary amine containing nucleic acid may be conjugated to the carboxylic acid groups on a coated polymer mediated by a coupling reagent such as EDAC. See, e.g., Yang et al., Small, 2009,5(2):235-43, hereby incorporated by reference. Other coupling methods are contemplated, e.g., the avidin/streptavidin-biotin interactions may be used, e.g., streptavidin may be coupled to the coated polymer surface and biotin may be linked to the cleaving nucleic acid.

Pharmaceutical Compositions

Generally, for pharmaceutical use, the compositions with the particle conjugates may be formulated as a pharmaceutical preparation comprising particle conjugates and a pharmaceutically acceptable carrier, diluent or excipient and/or adjuvant, and optionally one or more further pharmaceutically active compositions.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, e.g. about 10, 25, 50, 100, 200, 300 or 400 mg per unit dosage.

The compositions can be administered by a variety of routes including the oral, ocular, rectal, transdermal, subcutaneous, intravenous, intramuscular or intranasal routes, depending mainly on the specific preparation used. In certain embodiments, the disclosure contemplates intravenously-delivery of an aqueous saline buffer.

The embodiments will generally be administered in an "effective amount", by which is meant any amount of a composition that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

For an oral administration form, the composition can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compositions of the disclosure or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compositions, if desired with the substances customary therefore such as solubilizers, emulsifiers or further auxiliaries are brought into solution, suspension, or emulsion. The compositions can also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

In certain embodiments, it is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxy methylcellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxy groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release delivery systems. Particle conjugates can be entrapped in the poly(lactide-co-glycolide) microsphere depot by a number of methods, including formation of a water-in-oil emulsion with water and organic solvent (emulsion method), formation of a solid-in-oil suspension with particle dispersed in a solvent-based polymer solution (suspension method), or by dissolving the particle in a solvent-based polymer solution (dissolution method). One can attach poly(ethylene glycol) to particles (pegylation) to increase the in vivo half-life.

Targeting Moieties

Within certain embodiments, particles conjugated to cleaving nucleic acids further comprising a targeting moiety in order to target the particle to a physiological tissue or group of cells. Typically, diseased cells overexpress a specific cell surface marker, e.g., HER 2 for breast cancer cells. Antibodies or other molecules with binding affinity to these markers may be conjugated to the particles in order to restrict the movement of the particle to the location of the cells after administration.

In certain embodiments, the targeting moiety is a monoclonal antibody to HER-2, e.g., Herceptin, that targets HER-2 receptors for use in treating breast cancer. See Lee et al., Nat Med, 2007, 13:95-9; Artemov et al., Magn Reson Med, 2003, 49:403-8; and Huh et al., J Am Chem Soc, 2005, 127:12387-91, all hereby incorporated by reference in their entirety.

In certain embodiments, the targeting moiety is a monoclonal antibody-610 that targets a surface antigen for use in treating colon carcinoma. See Cerdan et al., Magn Reson Med, 1989, 12:151-63 1989, hereby incorporated by reference in its entirety.

In certain embodiments, the targeting moiety is an antibody to carcinoembryonic antigen (CEA) that targets CEA for use in treating colon tumors. See Tiefenauer et al., Magn Reson Imaging, 1996, 14:391-402, hereby incorporated by reference in its entirety.

In certain embodiments, the targeting moiety is a monoclonal antibody L6 that targets a surface antigen for use in treating intracranial tumor. See Remsen et al., Am J Neuroradiol, 1996, 17:411-18, hereby incorporated by reference in its entirety.

In certain embodiments, the targeting moiety is transferrin that targets transferrin receptor for use in treating carcinoma. See Kresse et al., Magn Reson Med, 1998, 40:236-42, hereby incorporated by reference in its entirety.

In certain embodiments, the targeting moiety is the EPPT peptide that targets underglycosylated mucin-1 antigen (uMUC-1) for use in treating breast, colon, pancreas and lung cancer. See Moore et al., Cancer Res, 2004, 64:1821-7, hereby incorporated by reference in its entirety.

In certain embodiments, the targeting moiety is folic acid that targets folate receptor for use in treating mouth carcinoma and cervical cancer. See Chen et al., PDA J Pharm Sci Technol, 2007, 61:303-13; Sun et al., Small, 2006, 4:372-9; and Sonvico et al., Bioconjug Chem, 2005, 16:1181-8, all hereby incorporated by reference in their entirety.

In certain embodiments, the targeting moiety is methotrexate that targets folate receptor for use in treating cervical cancer. See Kohler et al., Langmuir, 2005, 21:8858-64, hereby incorporated by reference in its entirety.

In certain embodiments, the targeting moiety is a monoclonal antibody A7 that targets colorectal tumor antigen for use in treating colorectal carcinoma. See Toma et al., Br J Cancer, 2005, 93:131-6, hereby incorporated by reference in its entirety.

In certain embodiments, the targeting moiety is chlorotoxin peptide that targets membrane-bound matrixmetalloproteinase-2 (MMP-2) for use in treating glioma. See Veiseh et al., Nano Lett, 2005, 5:1003-8, hereby incorporated by reference in its entirety.

In certain embodiments, the targeting moiety is F3 peptide that targets surface-localized tumor vasculature for use in treating glioma. See Reddy et al., Clin Cancer Res, 2006, 12:6677-86, hereby incorporated by reference in its entirety.

In certain embodiments, the targeting moiety is RGD or RGD4C that targets integrins for use in treating melanoma and epidermoid carcinoma. See Zhang et al., Cancer Res, 2007, 67:1555-62 and Uchida et al., J Am Chem Soc, 2006, 128:16626-33, both hereby incorporated by reference in their entirety.

In certain embodiments, the targeting moiety is luteinizing hormone releasing hormone (LHRH) that targets LHRH receptor for use in treating breast cancer. See Leuschner et al., Breast Cancer Res Treat, 2006, 99:163-76, hereby incorporated by reference in its entirety.

In certain embodiments, the targeting moiety is CREKA peptide that targets clotted plasma proteins for use in treating breast cancer. See Simberg et al., Proc Natl Acad Sci USA, 2007, 104:932-6, hereby incorporated by reference in its entirety.

In certain embodiments, the targeting moiety is an antibody to prostate specific membrane antigen (PSMA) that targets PSMA for use in treating prostate cancer. See Serda et al., Mol Imaging, 2007, 6:277-88, hereby incorporated by reference in its entirety.

In certain embodiments, the disclosure contemplates targeting moieties or proteins in any of the disclosed embodiments that are antibodies or fragments or chimera, antibody mimetics, or aptamers or any molecular entity that selectively binds targets that are more prevalent on cancer cells.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

The modular structure of antibodies makes it possible to remove constant domains in order to reduce size and still retain antigen binding specificity. Engineered antibody fragments allow one to create antibody libraries. A single-chain antibody (scFv) is an antibody fragment where the variable domains of the heavy ($V_H$) and light chains ($V_L$) are combined with a flexible polypeptide linker. The scFv and Fab fragments are both monovalent binders but they can be engineered into multivalent binders to gain avidity effects. One exemplary method of making antibodies and fragments includes screening protein expression libraries, e.g., phage or ribosome display libraries. Phage display is described, for example, in U.S. Pat. No. 5,223,409.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. U.S. Pat. No. 7,064,244.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. An antibody or fragment thereof may also be modified by specific deletion of human T cell epitopes or "deimmunization" by the methods disclosed in U.S. Pat. Nos. 7,125,689 and 7,264,806. Briefly, the heavy and light chain variable domains of an antibody can be analyzed for peptides that bind to MHC Class II; these peptides represent potential T-cell epitopes. For detection of potential T-cell epitopes, a computer modeling approach termed "peptide threading" can be applied, and in addition a database of human MHC class II binding peptides can be searched for motifs present in the VH and VL sequences. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. The V BASE directory provides a comprehensive directory of human immunoglobulin variable region sequences. These sequences can be used as a source of human sequence, e.g., for framework regions and CDRs. Consensus human framework regions can also be used, e.g., as described in U.S. Pat. No. 6,300,064.

Antibody mimetics or engineered affinity proteins are polypeptide based target binding proteins that can specifically bind to targets but are not specifically derived from antibody $V_H$ and $V_L$ sequences. Typically, a protein motif is recognized to be conserved among a number of proteins. One can artificially create libraries of these polypeptides with amino acid diversity and screen them for binding to targets through phage, yeast, bacterial display systems, cell-free selections, and non-display systems. See Gronwall & Stahl, J Biotechnology, 2009, 140(3-4), 254-269, hereby incorporated by reference in its entirety. Antibody mimetics include affibody molecules, affilins, affitins, anticalins, avimers, darpins, fynomers, kunitz domain peptides, and monobodies.

Affibody molecules are based on a protein domain derived from staphylococcal protein A (SPA). SPA protein domain denoted Z consists of three a-helices forming a bundle structure and binds the Fc protion of human IgG1. A combinatorial library may be created by varying surface exposed residues involved in the native interaction with Fc. Affinity proteins can be isolated from the library by phage display selection technology. See Orlova et al., Cancer Res., 2007, 67:2178-2186, hereby incorporated by reference in its entirety.

Monobodies, sometimes referred to as adnectins, are antibody mimics based on the scaffold of the fibronectin type III domain (FN3). See Koide et al., Methods Mol. Biol. 2007, 352: 95-109, hereby incorporated by reference in its entirety. FN3 is a 10 kDa, β-sheet domain, that resembles the $V_H$ domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955, hereby incorporated by reference in its entirety.

Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. See Skerra, FEBS J., 275 (2008), pp. 2677-2683, hereby incorporated by reference in its entirety.

The ankyrin repeat (AR) protein is composed repeat domains consisting of a β-turn followed by two α-helices. Natural ankyrin repeat proteins normally consist of four to six repeats. The ankyrin repeats form a basis for darpins (designed ankyrin repeat protein) which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The darpin libraries are typically denoted NxC, where N stands for the N-terminal capping unit, C stands for the C-terminal capping domain and x for the number of library repeat domains, typically between two to four. See Zahnd et al., J. Mol. Biol., 2007, 369:1015-1028, hereby incorporated by reference in its entirety.

Aptamers refer to affinity binding molecules identified from random proteins or nucleic acid libraries. Peptide aptamers have been selected from random loop libraries displayed on TrxA. See Borghouts et al., Expert Opin. Biol. Ther., 2005, 5:783-797, hereby incorporated by reference in its entirety. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. Nos. 5,475,096, and 5,270,163. The SELEX process provides a class of products which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric.

Terms

As used herein, "subject" refers to any animal, preferably a human patient, livestock, or domestic pet.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, the term "combined with" when used to describe the administration of particle conjugates and any additional treatment(s), e.g. anticancer agent, means that the additional treatment(s) may be administered prior to, together with, or after the administration of particle conjugates, or a combination thereof.

The term "polynucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The polynucleotide may be generated in any manner, including chemical synthesis, DNA replication, reverse transcription, or a combination thereof.

The term "oligonucleotide" generally refers to a short length of single-stranded polynucleotide chain usually less than 30 nucleotides long, although it may also be used interchangeably with the term "polynucleotide."

As used herein, the term "nucleic acid" refers to polynucleotides such as deoxyribonucleic acid (DNA), and, where appropriate, ribonucleic acid (RNA). The term should be understood to include either single- or double-stranded forms of nucleic acid, and, as equivalents, analogs of either RNA or DNA. Such nucleic acid analogs may be composed of nucleotide analogs, and, as applicable to the embodiment being described, may be single-stranded (such as sense or antisense) or double-stranded polynucleotides.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

EXPERIMENTAL

Synthesis and Characterization of 10-23 DNAzyme-Modified Gold Nanoparticles (AuNPs)

3'thiol-modified oligonucleotides (4 μM) were reduced and then mixed with AuNPs suspended at a final concentration of 8 nM. The solution was then stabilized with SDS and salted to 0.7 M NaCl over a period of 3 hours with intermittent sonication. The oligonucleotide density of the purified $DzT_{10}NPs$, where $T_{10}$ refers to the thiolated poly T spacer linking the DNAzyme to the nanoparticle, was 160±10 oligonucleotides/particle based on a fluorescence DNA quantification kit (Invitrogen). To verify particle integrity, TEM and UV-Vis analysis were performed before and after AuNP functionalization, and indicated that the particles remained dispersed following modification with DNAzymes. The catalytic activity of these particles was determined by measuring the rate of hydrolysis of a diribonucleotide within a DNA substrate that was functionalized with a 5' 6-fluorescein (FAME) and a 3' black hole quencher™ (BHQ™) (FIG. 1A).

Direct DNAzyme Conjugation to the Nanoparticle Surface and Impact on Catalytic Activity Liu & Lu disclose gold nanoparticle/DNAzyme assembly. See Chem. Mater., 2004, 16, 3231-3238. The DNAzyme is hybridized to linker strands that bridged the terminal sequences of DNA-functionalized nanoparticles, and therefore the DNAzymes were separated from the gold core. Hybridizing a large number of 8-17 DNAzymes onto the surface of DNA-modified AuNP aggregates significantly reduces the activity of the enzyme.

Figure 1B:
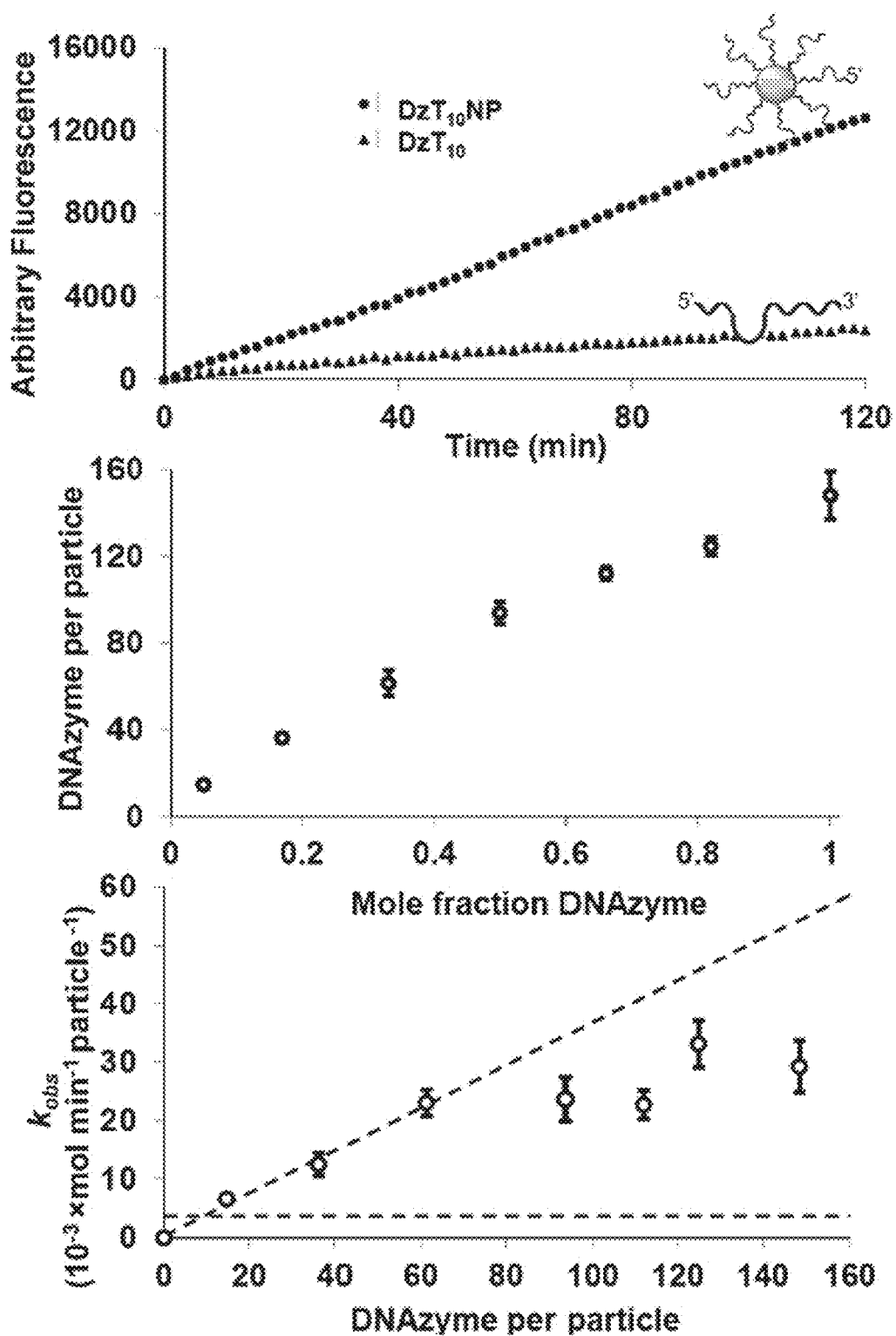
FIG. 1B is data. Top is a representative kinetic plot showing the rate of catalysis for 4.2 nM DzT10NP (closed circles) and DzT10 (triangles) en-zymes. Middle is a plot showing the DNAzyme surface density for T10 passivated DzNPs as a function of the mole fraction of DNAzyme added during the NP functionalization. Bottom is a plot showing kobs for the hydrolysis of a series of DzNPs that vary in DNAzyme surface density at [$Mg^{2+}$]=10 mM. The horizontal red line denotes the activity of free $DzT_{10}$ (4.2 nM). The diagonal dashed line is a best fit ($R_2$=0.99) through the lower density DzNP data points (≤60 DNAzymes/particle). All error bars represent the standard deviation of three measurements.
Figure 4:
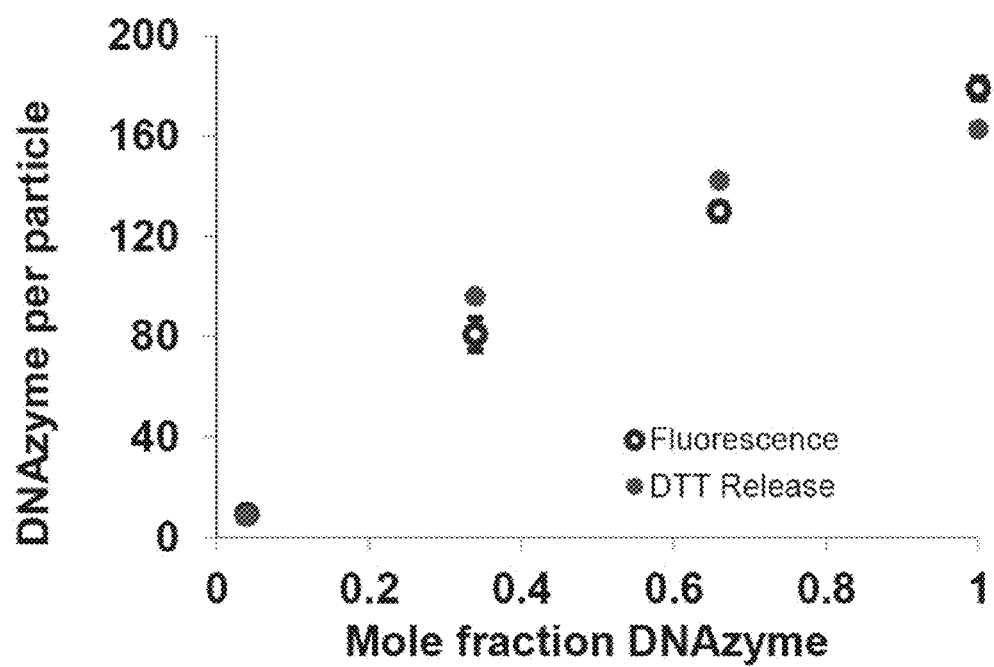
FIG. 4 is a plot showing the DNAzyme surface density of DzNPs as determined by two independent techniques. The first method is based on an oligonucleotide fluorescence quantification kit (open circles). The second approach measures the catalytic activity of DTT-released DNAzyme and quantifies the concentration using a standard calibration curve (red circles). Error bars represents the standard deviation of three measurements.
Figure 5:
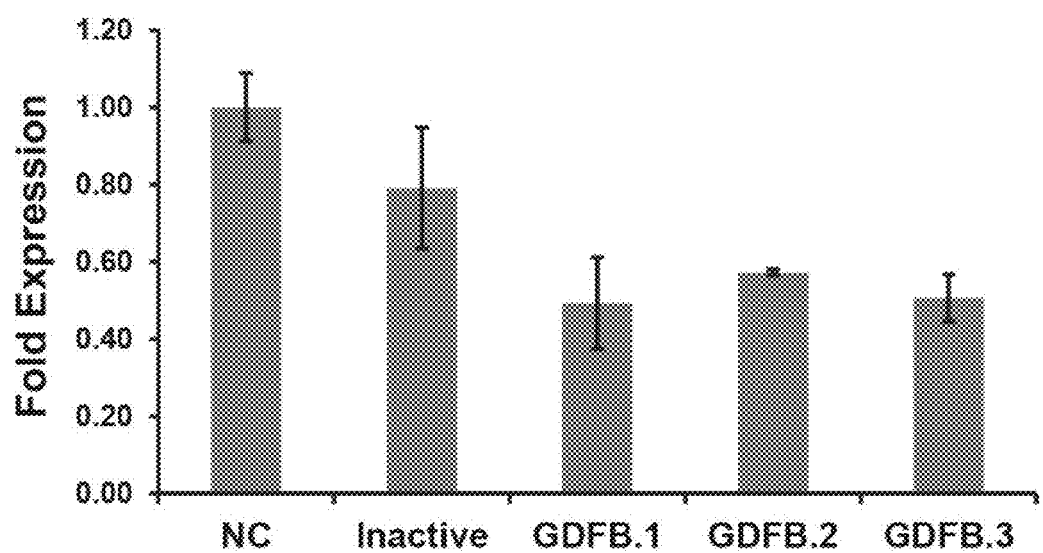
FIG. 5 shows data for DNAzyme-nanoparticle mediated knock down of GDF15. HCC1954 cells were treated with nanoparticles conjugated to DNAzyme for GDF15 at a concentration of 5 nM for 48 hrs. Total RNA was isolated and expression of GDF15 was determined by real-time PCR analysis. Values were normalized to housekeeping gene RPLPO. Fold expression relative to non-targeting control (NC) is shown. Error bars represent standard deviation between triplicates.
Figure 6:
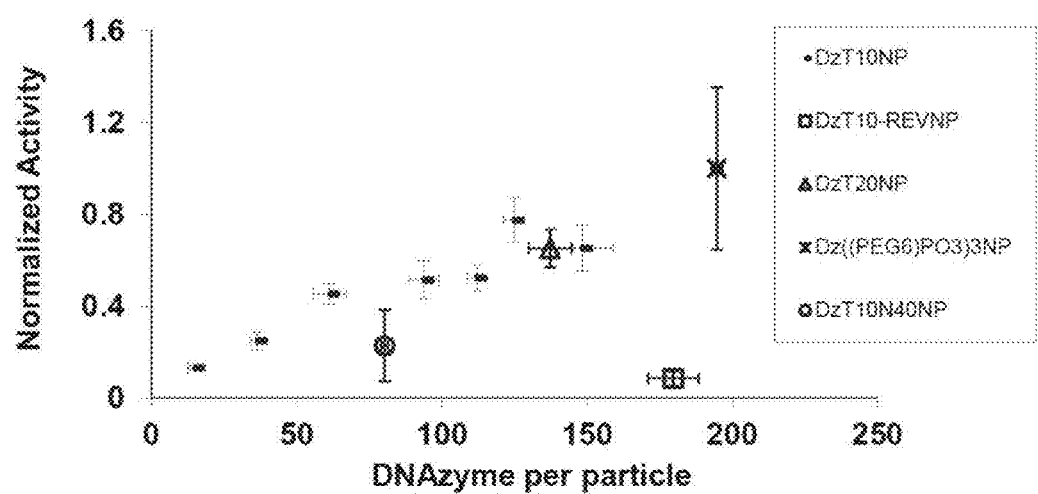
FIG. 6 shows data on the activity of DzNP synthesized using a variety of different linkers. The $k_{obs}$ values were normalized to the activity of $Dz((EG_6)PO_3)_3$NPs ([$MgCl_2$]=10 mM). Error bars are the standard deviation of three measurements.
Figure 7:
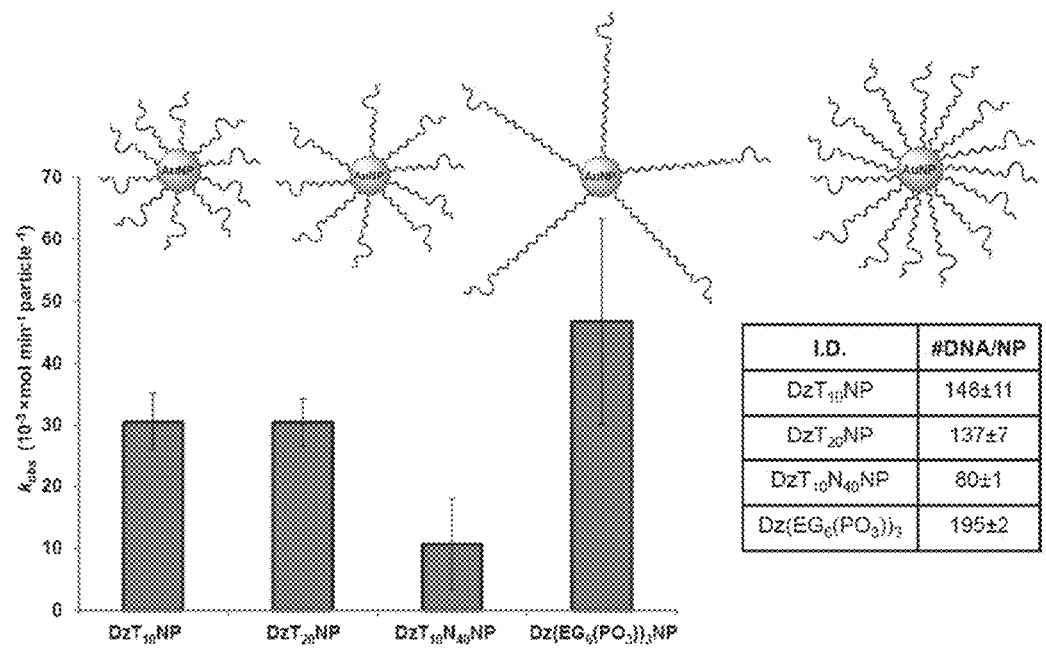
FIG. 7 shows data on the catalytic activity of DzNP synthesized using a variety of different linkers. The $k_{obs}$ values were normalized to the activity of $Dz((EG_6)PO_3)_3$NPs ([$MgCl_2$]=10 mM). Error bars are the standard deviation of three measurements.
Figure 8:
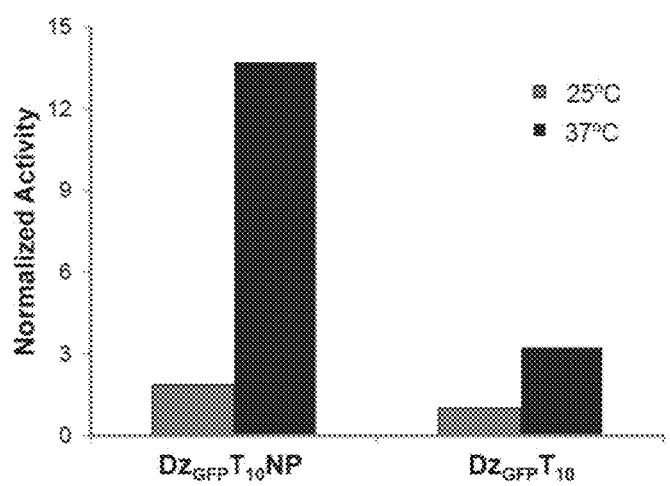
FIG. 8 shows a bar graph showing the normalized catalytic activity of $Dz_{GFP}T_{10}$NP (4.2 nM) and $Dz_{GFP}T_{10}$ (4.2 nM) normalized to $Dz_{GFP}T_{10}$ at 25° C.

Experiments were performed in order to determine if the sterically crowded oligonucleotide environment of an RNA-cleaving DzNP would inhibit catalysis. The reaction rate was measured using a temperature-controlled fluorometer, and reported in units of mol min$^{-1}$ by using a fluorescence calibration curve for a 3'FAM6 modified oligonucleotide standard. FIG. 1B top shows representative reaction kinetics for DzT$_{10}$NPs and free DzT$_{10}$ (See FIG. 4 for sequences) under certain conditions (25° C., 4.2 nM =[DzTio] and [DzT$_{10}$NP], 1 µM substrate, 20 mM Tris pH=7.4, 300 mM NaCl, 50 mM Mg$^{2-}$). The initial rate of the reaction was determined from the linear slope of the plot (t<80 min). The k$_{obs}$ for soluble DzT$_{10}$ and DzT$_{10}$NP were 0.017 and 0.095 mol min$^{-1}$, respectively. DzNP, rather than its individual sub-units, was compared to a single DNAzyme molecule. The nanoparticle functions as an ensemble entity inside living cells. For comparison, the individual enzymes sub-units in DzNPs showed an activity of 0.002 mole min$^{-1}$ when assuming a 33% hybridization efficiency. DzNPs are fairly stable under these conditions, and particles that were used in catalysis reactions for 12 hr only showed a 20% decrease in activity (as measured by the initial rate of reaction) when they were re-used the following day. This data indicates that the DzNPs are robust and retain catalytic activity despite the dense oligonucleotide environment on the surface of the nanoparticle.

Assemblies are Sensitive to DNAzyme Density and Orientation

To study the effect of surface packing density and steric crowding on the rate of catalysis, a series of DzNPs were synthesized using a binary mixture of two oligonucleotides that included a T$_{10}$ passivating sequence along with the DzT$_{10}$ (FIG. 1A). In this series, the total ssDNA concentration was kept constant while adjusting the molar concentrations of 3'thiol modified DzT$_{10}$ and T$_{10}$. Because both oligonucleotides have the same T$_{10}$ spacer, the DNA composition of AuNPs was expected to reflect that of the bulk solution. The goal was to tune the average spacing between adjacent DNAzymes and consequently tune steric crowding. The total number of DNA molecules per particle was measured using a commercial fluorescence assay (FIG. 1B middle). To further verify these measurements, DNA was released from the particle surface using dithiothreitol (DTT) and the DNAzyme concentration was determined by using the observed rate constant of substrate hydrolysis as compared to a calibration standard of soluble DNAzyme.

FIG. 1B bottom shows a plot of the initial rate constant of DzNP particles with a range of enzyme packing densities compared to soluble DNAzyme. At lower enzyme packing densities (15-60 enzymes/particle), the activity of each particle shows a linear increase as a function of the number of DNAzymes per particle. However, particles that have packing densities that exceed 60 DNAzymes per particle show saturation in activity. This trend indicates that steric packing limits the maximum activity of each DzNP assembly. As a corollary, this limit in maximum activity equates to each catalytic oligonucleotide providing a footprint of greater than ~11 nm$^2$ on the particle surface in order to achieve its full activity.

DNAzymes Catalytically Regulate Intracellular Gene Expression

Given that the hybridization efficiency and gene regulation efficacy have been shown to be dependent on the chemical nature of the group anchoring an oligonucleotide to an AuNP, the catalytic properties of DzNPs modified with the following poly T and ethylene glycol phosphate linkers: T$_{10}$, T$_{20}$, T$_{10}$N$_{40}$, and ((EG)$_6$PO$_3$)$_3$, were investigated. The measured oligonucleotide density for these fully packed particles was 148, 137, 80, and 195 oligonucleotides/particle for the T$_{10}$, T$_{20}$, T$_{10}$N$_{40}$, and ((EG)$_6$PO$_3$)$_3$ linkers, respectively. It was expected that longer linkers would generate DzNPs with increased catalytic efficiency, as this difference would be due to reduced steric inhibition for longer linkers. Surprisingly, no clear trend was observed for increasing linker length. In fact, DzT$_{10}$N$_{40}$NP (0.011 mol min$^{-1}$) had a slight decrease in activity when compared to DzT$_{10}$NP (0.03 mol min$^{-1}$) and DzT$_{20}$NP (0.03 of mol min$^{-1}$); whereas, DzT$_{10}$NP and DzT$_{20}$NP had identical activities. The ethylene glycol phosphate (EG)$_6$PO$_3$)$_3$ linker generated the most densely packed particles (~195 Dz molecules/AuNP), and when these particles were compared to DzT$_{10}$NP and DzT$_{20}$NP, they showed a 56% increase in k$_{obs}$. The results indicate that chemisorption of DNAzyme active site nucleobases to the gold surface alters their catalytic activity, and may play a significant role in tuning the catalytic activity of DzNPs, in addition to steric crowding (FIG. 1B).

Figure 2A:
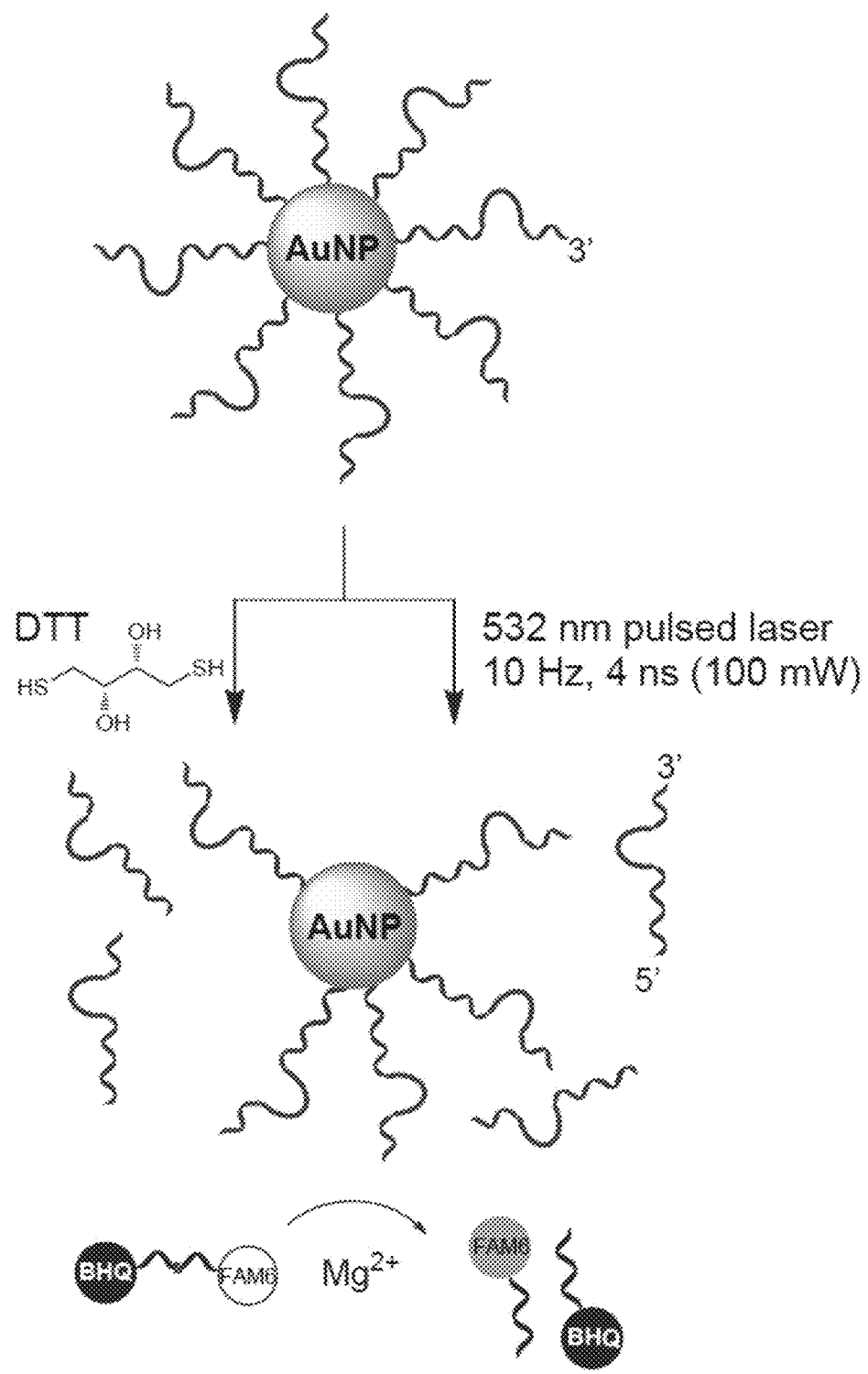
FIG. 2A illustrates and shows data on DNAzyme release from gold nanoparticles. Schematic showing DTT displacement (left) or laser irradiation (right) to release $Dz_{REV}T_{10}$ from the particle to enhance catalysis.
Figure 2B:
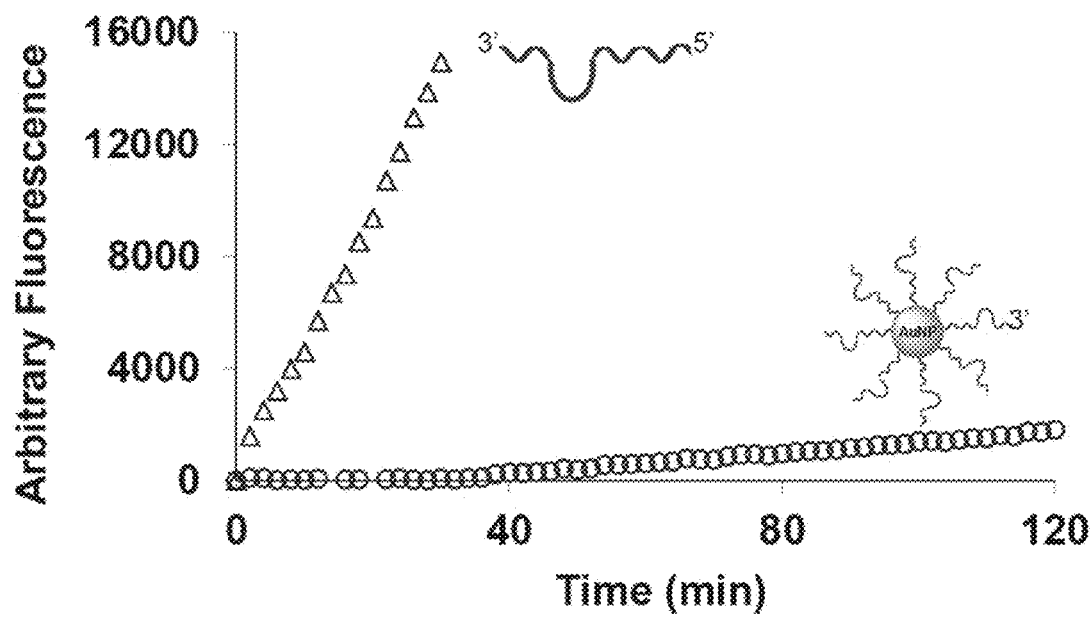
FIG. 2B is a kinetic plot showing rate of catalysis of $Dz_{REV}T_{10}$NP (open circles) and DTT displaced $Dz_{REV}T_{10}$ (open triangles) from the particle.

The role of non-specific interactions in DzNP catalytic activity was verified when the rate of substrate hydrolysis was measured using AuNPs functionalized with DNAzymes anchored through a 5' thiol (Dz$_{rev}$T10). DNA density on these particles was 180 oligonucleotides/AuNP, but we found that their activity was nearly abolished (FIG. 2A). Importantly, Dz$_{rev}$T$_{10}$NPs remained inactive even when their packing densities were reduced to 90 Dz/AuNP (~50% packed) either with or without T$_{10}$ passivation. Furthermore, when these particles are treated with mercaptoethanol, the Dz surface density is decreased, but again, the activity of the Dz$_{rev}$T$_{10}$NPs remained suppressed. When Dz$_{rev}$T$_{10}$NPs were treated with DTT in order to release the surface-bound DNA, the free DzT$_{10}$ fully recovered its activity, thus displaying a 3200% increase in catalytic activity (FIG. 2B). The drastic difference in activity between DzT$_{10}$NP and Dz$_{rev}$T$_{10}$NP (900% difference) indicates that the catalytic core is asymmetric in its sensitivity to the supporting gold nanoparticle surface. This observation agrees with systematic mutagenesis analysis studies on the 10-23 DNAzyme catalytic domain that have shown a high degree of sensitivity at many bases near the 5' terminus of the active site. Therefore, DNAzyme orientation needs to be carefully examined in DzNP design.

Photodynamic Release

Figure 2C:
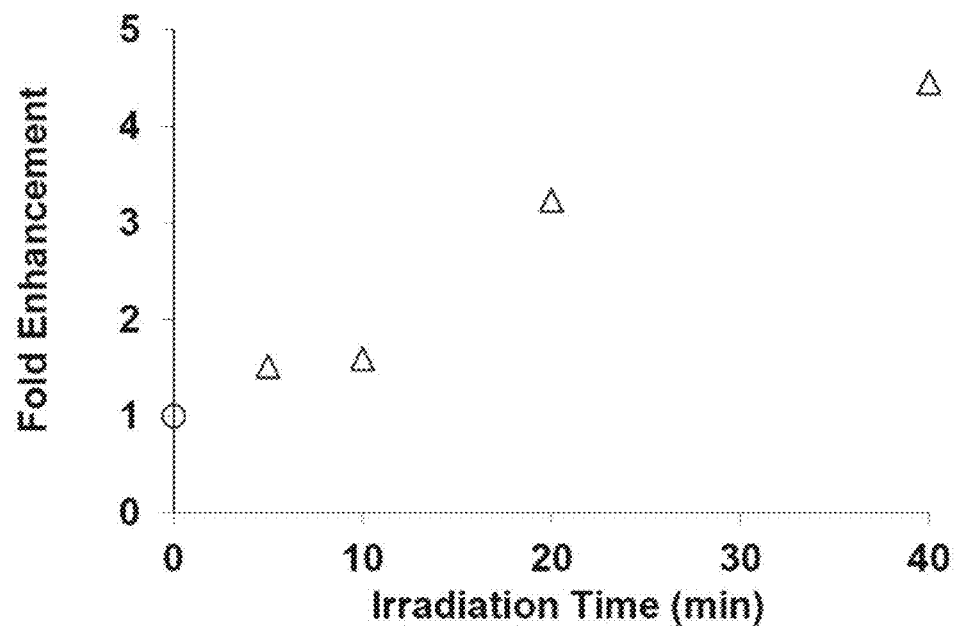
FIG. 2C is a plot showing $k_{obs}$ for the hydrolysis normalized to $Dz_{REV}T_{10}$NP for a series of particles irradiated at 532 nm for different times (intact particle=open circle and partially released Dz=open triangles: 10 Hz, 4 ns, 100 mW FIG. 3A shows data on gene regulation using DzNP. Top is a bar graph showing the relative catalytic activity of $DzT_{10}$ and $DzT_{10}$NP after exposure to DNase I for 120 min at 37° C.

Photodynamic control of gene regulation agents, DNAzymes specifically, is highly desirable, and various synthetic strategies have been employed to demonstrate this effect. Because the gold nanoparticle was found to inhibit the Dz anchored through its 5' terminus, photo-induced DNA release would be a suitable proof-of-concept to demonstrate this capability. Dz$_{rev}$T10 was released from the particle by irradiation with a 532 nm pulsed laser, which is known to selectively cleave the thiol-gold bond at certain laser powers (FIG. 2C). Importantly, this strategy offer significant advantages because it is synthetically facile and compatible with 2-photon and visible irradiation, which is in contrast to the recently developed azo-benzene and caged-nucleotide based approaches that require excitation at UV wavelengths.

DzNPs are Superior as a Gene Regulation Agent

Figure 3A:
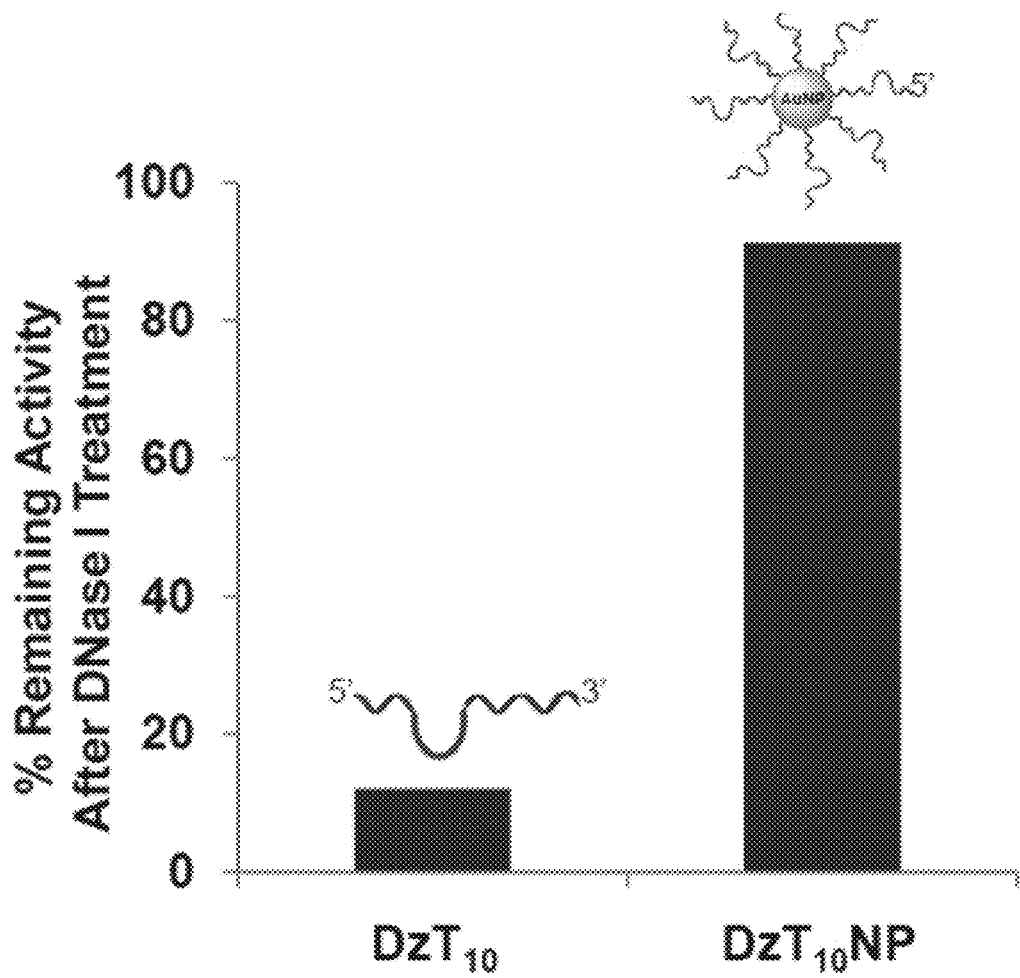
FIG. 3B shows data for a real-time PCR analysis of GDF15 mRNA expression of HCC1954 cells grown in a 12-well plate, which were treated with catalytic (DzGD-FNP) and non-catalytic (i-DzGDFNP) DzNPs targeting GDF15 mRNA and non-specific catalytic (DzNCNP) DzNPs at a NP concentration of 5 nM for 48 hrs.

To test DzNP resistance towards nucleases, the catalytic activity of free DzT$_{10}$ and DzT$_{10}$NP was measured before and after incubation with a model nuclease, DNase I. FIG. 3A shows that after DNase I treatment (120 min), the soluble enzyme retained only 10% of its original activity, while the DzNPs retained 90% of its original activity. Having confirmed the activity and nuclease resistance of DzNPs in vitro, experiments were performed to determine whether DzNPs can readily enter mammalian cells and catalytically regulate gene expression. To test this, $Dz_{GFP}$NPs were designed with recognition arms specific towards the green fluorescent protein (GFP) mRNA sequence expressed in a transiently transfected model HeLa cell line. Two 2' methyl ether linkages were incorporated within both the 5' and 3' termini of the DNA sequence in order to further reduce nuclease degradation. Flow cytometry was used to quantify the GFP expression levels on a per-cell basis in all samples.

Figure 3B:
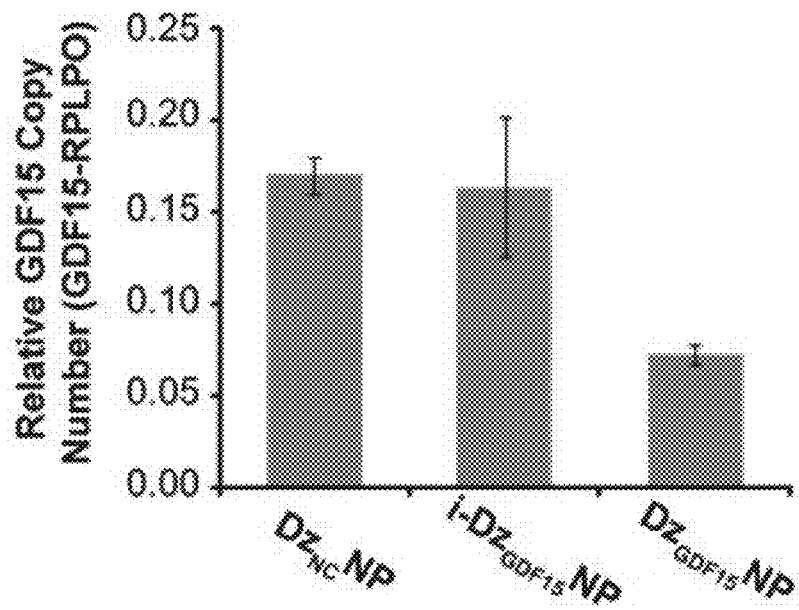

To distinguish between antisense and DNAzyme-catalyzed hydrolysis mechanisms, a single base mutation was introduced in the Dz catalytic core (G1 to A1) to generate catalytically inactive nanoparticles (i-$Dz_{GFP}$NP). The oligonucleotide density was quantified and found to be 83 and 99 DNAzymes per particle for i-$Dz_{GFP}$NP and $Dz_{GFP}$NP, respectively. HeLa cells were treated with (10 or 20) nM of $Dz_{GFP}$NP and i-$Dz_{GFP}$NP for 48 hrs, and then released from the cell culture flask and analyzed using flow cytometry. The average fluorescence intensity and standard deviation of triplicate wells are shown in FIG. 3B. The data indicates that the enzymatic nanoparticles reduce GFP expression in a dose-dependent manner for $Dz_{GFP}$NPs, whereas i-$Dz_{GFP}$NPs show little knockdown. Since both DNA-modified nanoparticles are complementary to the GFP mRNA, they are expected to reduce GFP expression levels through an antisense knockdown mechanism. Therefore, the difference in their activity of 20% can be attributed to the contributions of the DNAzyme catalytic core.

---

The invention claimed is:

1. A method of treating cancer comprising administering an effective amount of a pharmaceutical composition, to a subject in need thereof,
   wherein the pharmaceutical composition comprises particle conjugated to a catalytically cleaving nucleic acid;
   wherein the catalytically cleaving nucleic acid comprises a DNAzyme sequence having SEQ ID NO:1;
   wherein conjugation to the particle is through the 3' end of DNAzyme; and
   wherein the catalytically cleaving nucleic acid is conjugated to a cancer cell targeting moiety.

2. The method of claim 1 wherein the targeting moiety is an antibody that targets a tumor antigen.

3. The method of claim 1 wherein the targeting moiety is antibody to HER-2.

4. The method of claim 1 wherein the targeting moiety is an antibody to carcinoembryonic antigen.

5. The method of claim 1 wherein the targeting moiety is transferrin.

6. The method of claim 1 wherein the targeting moiety is folic acid.

7. hod of claim 1 wherein the targeting moiety is methotrexate.

8. The method of claim 1 wherein targeting moiety is luteinizing hormone releasing hormone.

9. The method of claim 1, wherein the targeting moiety is a nucleic acid sequence functioning to hybridize to a target of interest.

10. The method of claim 1, wherein the targeting moiety is a nucleic acid sequence that hybridizes to c-Jun mRNA.

11. The method of claim 1, wherein the targeting moiety is a nucleic acid sequence that hybridizes to LMP1 mRNA.

12. The method of claim 1, wherein the targeting moiety is a nucleic acid sequence that hybridizes to mRNA of human telomere reverse transcriptase.

13. The method of claim 1, wherein the targeting moiety is a nucleic acid sequence that hybridizes to survivin mRNA.

14. The method of claim 1, wherein the targeting moiety is a nucleic acid sequence that hybridizes to a translation initiation region of c-myc RNA.

15. The method of claim 1, wherein the cancer is selected from brain, lung, cervical, ovarian, colon, breast, gastric, skin, ovarian, pancreatic, prostate, neck, and renal cancer.

16. The method of claim 1, wherein, the pharmaceutical composition is administered in combination with a second anticancer agent.

17. The method of claim 16 wherein, the second anticancer agent may be selected from temozolamide, bevacizumab, procarbazine, lomustine, vincristine, gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vinblastine, vindesine, vinorelbine, taxol, taxotere, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, combretastatin, thalidomide, and/or lenalidomide or combinations thereof.

18. The method of claim 1, wherein the subject is exposed to electromagnetic radiation under conditions such that the administered particle releases nucleic acids conjugated to the particle.

* * * * *

SEQUENCE LISTING

<160> NUMBER OF SEQ ID NOS: 9

<210> SEQ ID NO 1
<211> LENGTH: 15
<212> TYPE: DNA
<213> ORGANISM: Artificial
<220> FEATURE:
<223> OTHER INFORMATION: Synthetic

<400> SEQUENCE: 1
ggctagctac aacga                                                    15

<210> SEQ ID NO 2
<211> LENGTH: 28
<212> TYPE: DNA
<213> ORGANISM: Artificial
<220> FEATURE:
<223> OTHER INFORMATION: Synthetic

<400> SEQUENCE: 2
gcacccaggc tagctacaac gactctct                                      28

<210> SEQ ID NO 3
<211> LENGTH: 15
<212> TYPE: DNA
<213> ORGANISM: Artificial
<220> FEATURE:
<223> OTHER INFORMATION: Synthetic

<400> SEQUENCE: 3
gagagagaug ggtgc                                                    15

<210> SEQ ID NO 4
<211> LENGTH: 15
<212> TYPE: DNA
<213> ORGANISM: Artificial
<220> FEATURE:
<223> OTHER INFORMATION: Synthetic

<400> SEQUENCE: 4
acccaagaag gggtg                                                    15

<210> SEQ ID NO 5
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: N

```
<222> LOCATION: (1)..(9)
<223> OTHER INFORMATION: N is any nucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 5
gcntnacnnn at                                                              12

<210> SEQ ID NO 6
<211> LENGTH: 18
<212> TYPE: DNA
<213> ORGANISM: Artificial
<220> FEATURE:
<223> OTHER INFORMATION: Synthetic

<400> SEQUENCE: 6
aattccgtag gtccagtg                                                        18

<210> SEQ ID NO 7
<211> LENGTH: 14
<212> TYPE: DNA
<213> ORGANISM: Artificial
<220> FEATURE:
<223> OTHER INFORMATION: Synthetic

<400> SEQUENCE: 7
atctcctcct gttc                                                            14

<210> SEQ ID NO 8
<211> LENGTH: 10
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t

<400> SEQUENCE: 8 nagcntcgaa                                                                 10

<210> SEQ ID NO 9
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
```

```
<400> SEQUENCE: 9
tnagcntcga aatagt                                                          16
```